United States Patent
Okawa et al.

(10) Patent No.: US 6,458,392 B1
(45) Date of Patent: Oct. 1, 2002

(54) PREVENTIVE, ALLEVIATIVE OR REMEDY FOR HYPERTENSION

(75) Inventors: Wataru Okawa, Tokyo (JP); Yuki Mitsui, Tokyo (JP); Takuya Watanabe, Tokyo (JP); Yasuteru Eguchi, Tokyo (JP); Hirokazu Takahashi, Tokyo (JP); Atsushi Suzuki, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/901,909

(22) Filed: Jul. 11, 2001

(30) Foreign Application Priority Data

Jul. 12, 2000 (JP) ........................................ 2000-210865

(51) Int. Cl.$^7$ ............................................... A61K 35/78
(52) U.S. Cl. ..................... 424/776; 424/725; 426/629
(58) Field of Search ................. 424/776, 725; 426/629

(56) References Cited

U.S. PATENT DOCUMENTS

| | | | | |
|---|---|---|---|---|
| 3,845,220 A | * | 10/1974 | Suzuki et al. | 424/776 |
| 5,045,334 A | * | 9/1991 | Kopsch et al. | 426/422 |
| 5,132,135 A | * | 7/1992 | Schweinfurth | 426/385 |
| 5,932,623 A | | 8/1999 | Tanabe et al. | 514/731 |
| 5,994,413 A | | 11/1999 | Tanabe et al. | 514/732 |

FOREIGN PATENT DOCUMENTS

| | | |
|---|---|---|
| JP | 4-145048 | 5/1992 |
| JP | 4-145049 | 5/1992 |
| JP | 8-259453 | 10/1996 |

OTHER PUBLICATIONS

Salvaggio et al., Journal of Hypertension 8(6): 585–590 (1990). Abstract.*
Periti et al., Clinical Science (London) 72(4): 443–448 (1987). Abstract.*
Tse, Journal of Pharmaceutical Sciences 81(5): 449–452 (1992). Abstract.*
Li et al., Zhongyao Tongbao 11(8): 489–490 (1986). Abstract.*
Cheng et al., Chinese Pharmaceutical Journal 46(6): 575–582 (1994). Abstract.*
Food Research Results Information, No. 9, pp. 20–21, "Inhibition of Angiotensin I Converting Enzyme by the Storage Root of Sweet Potato", 1997 (with English translation).

* cited by examiner

Primary Examiner—Jean C. Witz
(74) Attorney, Agent, or Firm—Oblon, Spivak, McClelland, Maier & Neustadt, P.C.

(57) ABSTRACT

Provided is a preventive, ameliorant or remedy for hypertension excellent in both blood pressure lowering action and blood pressure-rise suppressing action and having high safety.

This preventive, ameliorant or remedy for hypertension comprises a coffee bean extract.

17 Claims, No Drawings

PREVENTIVE, ALLEVIATIVE OR REMEDY FOR HYPERTENSION

TECHNICAL FIELD

The present invention relates to a preventive, alleviative or remedy for hypertension which has excellent blood pressure lowering effects, blood-pressure-rise suppressing effects and safety and is available in the form of a food or pharmaceutical.

BACKGROUND ART

Examples of a pharmaceutical used for treatment of hypertension include various neuroleptics acting on the neural-factor-related regulator system, ACE inhibitors acting on the heurohumoral-factor-related regulator system, AT receptor antagonists, Ca antagonists acting on the vascular-endothelium-derived-substance-related regulator system, and hypotensive diuretics acting on the body-fluid-regulator system in the kidney. These pharmaceuticals are mainly used in medical institutions for patients suffering from severe hypertension.

Under the present state, however, pharmaceuticals used as a measure against hypertension are a serious burden for patients because in spite of satisfactory effectiveness, their side effects are not a few.

In the case where hypertension is regarded as a life-style related disease, on the other hand, general therapies for improving the life style such as dietetic therapy, kinesitherapy and limitation of alcoholic intake or smoking are applied widely not only to the people having a high normal blood pressure including a mild case but also to patients suffering from severe hypertension. With a tendency to recognize the importance of general therapies, improvement of eating habits has received great attention. Since there exist a large number of foods having blood pressure lowering action, pressure reducing materials derived from foods have so far been briskly searched for and separation and identification of their effective ingredients have been carried out frequently.

Under such situations, there is an increasing demand for the development of a method for preventing, ameliorating or treating hypertension without depending on pharmaceuticals if possible. As such a method, dietetic therapy is particularly important, so that foods having blood pressure lowering effects or blood-pressure-rise inhibitory effects have briskly been searched for. Proposed is use of, as a hypotensor, the juice of an unripe fruit of apples, pears, peaches or like fruits belonging to the family Rosaceae which juice contains fruit polyphenol such as caffeine acid having angiotensin I converting enzyme (ACE) inhibiting action (Japanese Patent Application Laid-Open (Kokai) No. Hei 8-259453). It is also reported that a water extract of sugarcane root tuber contains a chlorogenic acid, which is a polyphenol, and it has ACE inhibitory action (Food Research Results Information, No. 9, 20-21(1997)).

Foods which are said to have pressure reducing effects or their effective ingredients, however, tend to be not always satisfactory in their effectiveness, intake frequency or taste upon intake and in addition, many of them do not start exhibition of blood pressure lowering effects soon after intake.

An object of the present invention is therefore to provide a preventive, alleviative or remedy for hypertension which is derived from plants or foods, has excellent safety, does not become a burden for patients when administered daily and orally, and has high antihypertensive action.

DISCLOSURE OF THE INVENTION

The present inventors have searched for various food- or plant-derived components useful for the prevention or amelioration of hypertension. As a result, it has been found that an extract of coffee beans containing caffeine which is a stimulant has high pressure reducing action and can suitably be formed into a pharmaceutical or food.

In the present invention, there is thus provided a preventive, ameliorant or remedy for hypertension, which comprises an extract of coffee beans; and a food containing the extract.

BEST MODE FOR CARRYING OUT THE INVENTION

The extract of coffee beans to be used in the present invention is an extract from coffee beans which are fruits of a coffee tree. As the coffee tree, any one of *C. arabica, C. robusta, C. liberica* and *C. arabusta* is usable.

As the coffee beans to be extracted in the present invention, either raw beans or decaffeine treated beans or roasted beans are usable, with raw beans being particularly preferred.

Examples of the method for extracting, from coffee beans, an ingredient effective for the prevention, amelioration or treatment of hypertension include solvent extraction and supercritical fluid extraction. The extract obtained from coffee beans may be purified or may be adjusted by treatment with an ion exchange resin or the like (for example, Japanese Patent Application Laid-Open (Kokai) No. Hei 4-145048, Japanese Patent Application Laid-Open (Kokai) No. Hei 4-145049, etc.).

Examples of the extracting solvent used for solvent extraction include water and hydrophilic organic solvents such as methanol, ethanol, 2-propanol, acetone and methyl ethyl ketone. As the extracting solvent, a water-containing hydrophilic organic solvent having a water content of 5 wt. % (which will hereinafter be called %, simply) or greater, particularly, hydrous ethanol.

The extract of coffee beans to be used in the present invention contains various substances such as known already for example polysaccharides, lipids, chlorogenic acids, proteins, caffeine, minerals and fatty acids etc. It preferably contains chlorogenic acids and caffeine at a weight ratio of 2 or greater, preferably 2 to 1000, more preferably 2.5 to 500, especially 2.5 to 100 from the viewpoints of effects for preventing, ameliorating or treating hypertension, and sour taste with astringency upon intake. Caffeine suppresses pungency and chlorogenic-acid-induced sourness, whereby such a taste is attained. The components of the coffee bean extract may be adjusted to fall within the above-described range by the addition of chlorogenic acid or caffeine.

Examples of the chlorogenic acid include those having caffeine acid ester-bonded to one or two hydroxy groups, at the 3-, 4- or 5-position of quinic acid. Specific examples include 3-caffeoylquinic acid (chlorogenic acid) having caffeine acid ester-bonded to the hydroxyl group at the 3-position of quinic acid; 5-caffeoylquinic acid having caffeine acid ester-bonded to the hydroxyl group at the 5-position of quinic acid; 4-caffeoylquinic acid (cryptochlorogenic acid) having caffeine acid ester-bonded to the hydroxyl group at the 4-position of quinic acid; and isochlorogenic acids having caffeine acid ester-bonded to two hydroxyl groups, among hydroxyl groups at the 3-, 4- and 5-positions of quinic acid (ex. 3,5-caffeoylquinic acid).

Salts of them are also embraced in the term "chlorogenic acid" used herein.

No particular limitation is imposed on the salts of a chlorogenic acid insofar as they are pharmaceutically acceptable salts. Examples include salts of an alkali (alkaline earth) metal such as sodium, potassium, calcium and magnesium. The chlorogenic acid exists also as a salt in naturally-occurring substances.

The preventive, ameliorant or remedy for hypertension according to the present invention may further contain another antihypertensive (agents) materials (such as α-blocker, β-blocker, αβ-blocker, ACE inhibitor, angiotensin II receptor antagonist, Ca blocker, diuretic, or psychotropic agent); vitamin (such as Vitamin A, Vitamin $B_1$, $B_2$, $B_6$, $B_{12}$, Vitamin C, Vitamin D or Vitamin E); and another active ingredient having blood pressure lowering action [physiologically active substance (ex. high unsaturated fatty acids of ω-3 type such as α-linolenic acid, EPA or DHA, triglyceride and/or diglyceride having this fatty acid as a component fatty acid, catechin which is a tea polyphenol or polymer thereof, or rutin which is a buckwheat polyphenol), Litchi Chinensis Sonn., ginkgo tree, Zizyphi Fructus, Polygonati Rhizoma, Cassiae Semen, *Cortinellus shiitake, Momovdicae grosvenori,* flowers of *Chrysanthemum morifolium,* leaves of *Samallanthus sonchifolius,* mulberry leaves, leaves of Banaba (*Lagestroemia speciosa*), Senpo, *Plantaginis semen,* and these extract etc.]

When used as a medicament, the preventive, ameliorant or remedy for hypertension according to the present invention can be formed into an oral administrable composition by adding thereto a pharmaceutically acceptable carrier. Examples of the oral administrable composition include tablets, granules, fine subtilaes, pills, powders, capsules (hard capsules and soft capsules), troches, chewables and liquid preparations (medical drink).

The preventive, ameliorant or remedy for hypertension according to the present invention is available as a food by adding thereto another component. Examples include foods in a liquid, emulsion or paste form such as beverage, soy sauce, milk, yogurt and miso to which ordinarily employed food additives have been added; semi-solid foods such as jelly and gummy; solid foods such as gum, tofu and supplement; powdery foods. Although it is available in any form, beverages, particularly soft drinks, are preferred.

An effective administration amount of the coffee bean extract of the present invention is preferably 5 to 5000 mg, especially 10 to 500 mg, a day per adult (weight: 60 kg) in terms of a chlorogenic acid contained in a dry solid content of the coffee bean extract.

EXAMPLES

Preparation of the Extract from Coffee Beans

From "Flavor Holder FH1041" (trade name of a food additive; product of T. Hasegawa Co., Ltd.; Coffee Bean Extract 3), an eluate was obtained using a cationic exchange column (for example, "SK-1B", trade name; product of Mitsubishi Chemical Co., Ltd.), followed by concentration into Coffee Bean Extract 4. Caffeine was extracted from the column and the extract was added to the coffee bean extract for ingredient adjustment, whereby Coffee Bean Extracts 1 and 2 were prepared.

The dry solid contents of Coffee Bean Extracts prepared by the above-described process and amounts of chlorogenic acid and caffeine contained in them are shown in Table 1.

TABLE 1

|  | Dry solid content (%) | Chlorogenic acid/ caffeine contained in Coffee Bean Extract | |
| --- | --- | --- | --- |
|  |  | Total (%) | Ratio |
| Coffee Bean Extract 1 | 71 | 51 | 1.2 |
| Coffee Bean Extract 2 | 58 | 39 | 2.5 |
| Coffee Bean Extract 3 | 53 | 34 | 4.8 |
| Coffee Bean Extract 4 | 48 | 29 | 28.0 |

Example 1

(a) Animals Provided for Test

Evaluation test was started after blood pressure of each of male, 12 week old, spontaneously hypertensive rats (SHRs) was preliminarily measured for successive 7 days by using a commercially available noninvasive sphygmomanometer for rat (manufactured by Softlon Co., Ltd.) in order to accustom the rat to sphygmomanometric operation. These rats were all bred under conditions (breeding room in a rat region) of room temperature at 25±1° C., humidity of 55±10% RH and illumination for 12 hours (from 7:00 am to 7:00 pm).

(b) Administration Method and Amount

As a material to be administered, Coffee Bean Extract 1, Coffee Bean Extract 2, Coffee Bean Extract 3 and Coffee Bean Extract 4 were used in Test Group 1, Test Group 2, Test Group 3 and Test Group 4, respectively. Coffee Bean Extracts 1, 2, 3 and 4 were each dissolved in 0.85% physiological saline to give a dry solid content of 100 mg/kg. In Test Group 5, Coffee Bean Extract 1 was dissolved in 0.85% physiological saline to give a dry solid content of 150 mg/kg. As a control group, 0.85% physiological saline was employed. Each of them was forcedly administered p.o. by using a metal stomach tube. The dosage was 5 ml/rat.

(c) Test Method

SHRs which had been fasted overnight were employed for the test in groups, one group consisting of 6 rats. Systolic blood pressures of the caudal artery prior to oral administration and 6 hours after administration were measured.

(d) Statistic Treatment Method

Measurement results are indicated by mean and standard error. As a result of Student's t-test, the significant level was designated as 5% or less.

Systolic blood pressures prior to oral administration and 6 hours after administration are shown in Table 2. As is apparent from Table 2, the blood pressure showed a significant decline in the test groups to which the coffee bean extract had been administered compared with that in the control group and improvement was recognized.

TABLE 2

|  | Administered | Systolic blood pressure (SBP) (mmHg) | |
| --- | --- | --- | --- |
|  |  | Prior to administration | Six hours after administration |
| Control group | — | 196.0 ± 2.1 | 200.6 ± 2.1 |
| Test group 1 | Coffee Bean Extract 1 | 198.8 ± 1.1 | 197.4 ± 2.3 |
| Test group 2 | Coffee Bean Extract 2 | 200.7 ± 1.6 | 196.0 ± 1.6* |
| Test group 3 | Coffee Bean Extract 3 | 201.0 ± 1.8 | 192.6 ± 1.3* |

TABLE 2-continued

|  | Administered | Systolic blood pressure (SBP) (mmHg) | |
|---|---|---|---|
|  |  | Prior to administration | Six hours after administration |
| Test group 4 | Coffee Bean Extract 4 | 200.7 ± 1.9 | 186.8 ± 3.9* |
| Test group 5 | Coffee Bean Extract 5 | 198.4 ± 2.7 | 199.4 ± 0.8 |

*The significance level relative to the control group was 5% or less, meaning existence of a significant difference.

Example 2

Blood Pressure Reduction Test on Volunteer

Blood pressure lowering performance of a soft drink beverage containing Coffee Bean Extract 3 was evaluated by in thirties six male volunteers by cross matching at 2 weeks intervals.
1) Tested Materials and Test Method In accordance with Example 7, two soft drinks, one (P) free of Coffee Bean Extract 3 and the other (S) containing it, were prepared and they were confirmed to have equal flavor and taste. While blindfolding, these volunteers took one bottle (100 ml) of the drink (P) everyday for two weeks and then one bottle (100 ml) of the drink (S) everyday for 2 weeks, 4 weeks in total, at any time.
2) Measurement of Blood Pressure The blood pressure was measured using "HEM609" (trade name), a blood pressure monitor manufactured by Omron Corporation. In consideration of variations of blood pressure within a day, blood pressure was measured, after rest for 10 minutes before measurement, at a predetermined time of a day, both prior to drinking and two weeks after starting of drinking.

The mean blood pressure before the test was 141 mmHg (systolic).

A decline in systolic blood pressure two weeks after drinking is shown in Table 3. It has been recognized that the blood pressure showed a significant decline in the group taking the soft drink containing the coffee bean extract of the present invention.

TABLE 3

|  | Soft drink | A decline in systolic blood pressure two weeks after drinking (mmHg) |
|---|---|---|
| Control | P | 1.2 ± 1.6 |
| Test group | S | 8.7 ± 1.9* |

*A significance level was 5% or less relative to the control group, meaning existence of a significant difference.

Example 3

Powdery Food

Water was added to 47.4% of glucose, 10% of gum arabic, 36% of dextrin, 2% of citric acid, 1% of Vitamin C and 3.6% of a coffee bean extract ("Flavor Holder FH1041", trade name; product of T. Hasegawa Co., Ltd.) to dissolve the latter in the former. The resulting solution was spray dried by a spray drier. A sufficient amount of a flavor (lemon flavor) was added to the resulting powder, followed by uniform mixing. The mixture was dispensed into 10 g portions, whereby powdery food containing the coffee bean extract as a preventive, ameliorant or remedy for hypertension and drinkable after dissolved in water or hot water was prepared.

Example 4

Sugar Tablet Candy

Uniformly mixed were 76.4% of anhydrous glucose (crystalline), 9% of frost sugar, 4.5% of orange flavor powder, 2% of guar gum, 2.5% of ascorbic acid, 1.5% of citric acid (crystals), 3.6% of a coffee bean extract ("Flavor Holder FH1041" trade name; product of T. Hasegawa Co., Ltd.), 0.5% of sucrose fatty acid ester (HLB 20) and a sufficient amount of a colorant. The resulting mixture was tableted in a conventional manner into tablets, each weighing 2 g and having a diameter of 15 mm φ, whereby sugar tablet candies having a good taste and containing the coffee bean extract as a preventive, ameliorant or remedy for hypertension were prepared.

Example 5

Food Made of Wheat Flour (Cup Cake)

Using 100 g of soft flour, 100 g of chicken egg, 110 g of sugar, 25 g of shortening, 35 g of margarine, 2.5 g of baking powder, 6.0 g of a liquor, 3.6 of a coffee bean extract ("Flavor Holder FH1041" trade name; product of T. Hasegawa Co., Ltd.) and a sufficient amount of water, a dough for cup cake was prepared. The resulting dough was dispensed into 10 cup cake molds, followed by baking in a conventional manner, whereby cup cakes having a good taste and containing the coffee bean extract as a preventive, ameliorant or remedy for hypertension were obtained.

Example 6

Jellies

After mixing 0.65% of a mixed gelling agent of carrageenan and locust bean gum, 5.0% of a 50% concentrated juice of grapefruit, 0.05% of citric acid, 0.05% of Vitamin C and 1.8% of a coffee bean extract ("Flavor Holder FH1041" trade name; product of T. Hasegawa Co., Ltd.), the balance of water was added to the mixture to dissolve the latter in the former. A small amount of a grapefruit flavor was added. After sterilization by keeping the mixture at 85° C. for 5 minutes, it was dispensed into 100 ml containers. They were allowed to stand for 8 hours and then gradually cooled to 5° C. for gelation, whereby jellies melting well in the mouth, having a fruit taste and good feeling upon eating and containing the coffee bean extract as a preventive, ameliorant or remedy for hypertension were obtained.

Example 7

Soft Drink

Water was added to 13% of inverted fructose/glucose syrup, 0.3% of citric acid, 0.03% of ascorbic acid, 0.02% of sodium citrate, 0.1% of flavor (lime flavor) and 0.36% of a coffee bean extract ("Flavor Holder FH1041" trade name; product of T. Hasegawa Co., Ltd.) to dissolve the latter in the former, whereby 5 liters of the solution was obtained as a beverage. Into glass bottles, 100-ml portions of the resulting solution were poured, followed by sterilization in a conventional manner, whereby soft drinks having a good taste and containing the coffee bean extract as a preventive, ameliorant or remedy for hypertension were obtained.

Example 8

Sugarless Drink

After adding 360 mg of a coffee bean extract ("Flavor Holder FH1041" trade name; product of T. Hasegawa Co., Ltd.) to, as a commercially available sugarless drink, Oolong tea (product of Suntory, Ltd.) and dissolving the former in the latter, the solution was sterilized in a conventional manner, whereby a sugarless drink having a good taste and containing the coffee bean extract as a preventive, ameliorant or remedy for hypertension was obtained.

Example 9

Medical Vitamin Drink

To a sufficient amount of purified water were added 800 mg of taurine, 11000 mg of sucrose, 50 mg of caramel, 30 mg of sodium benzoate, 5 mg of vitamin $B_1$ nitrate, 20 mg of Vitamin $B_2$, 20 mg of Vitamin $B_6$, 2000 mg of Vitamin C, 100 mg of Vitamin E, 2000 I.U. of Vitamin $D_3$, 20 mg of nicotinic acid amide and 360 mg of a coffee bean extract ("Flavor Holder FH1041" trade name; product of T. Hasegawa Co., Ltd.) to dissolve the latter in the former. After adjustment of pH to 3 with an aqueous solution of phosphoric acid, purified water was added to give a total amount of 50 mL. The resulting aqueous solution was sterilized at 80° C. for 30 minutes, whereby a medical drink free of a component change after storage, having excellent taste and flavor and containing the coffee bean extract as a preventive, ameliorant or remedy for hypertension was obtained.

Example 10

Chewable Tablets

To 99 parts by weight of chewable tablet powder composed of 15% of a vitamin mixed preparation containing Vitamin $B_1$ nitrate, Vitamin $B_2$, Vitamin $B_6$ and Vitamin C, 59.6% of frost sugar, 20.9% of dextrin, 3% of sucrose ester, 1.0% of hydroxypropyl cellulose and 0.5% of flavor, was added 8.6 parts by weight of a coffee bean extract ("Flavor Holder FH1041" trade name; product of T. Hasegawa Co., Ltd.). The resulting mixture was tableted in a conventional manner into tablets, each 0.2 g in weight, whereby chewable tablets excellent in both taste and flavor and containing the coffee bean extract as a preventive, ameliorant or remedy for hypertension were obtained. One dose requires 5 tablets.

Example 11

Soy Sauce

To a commercially-available salt-reduced soy sauce (100 parts by weight of salt-reduced say sauce produced by Kikkoman Corporation), 1.8 parts of a coffee bean extract ("Flavor Holder FH1041" trade name; product of T. Hasegawa Co., Ltd.) was added to dissolve the latter in the former, followed by sterilization, whereby a soy sauce free of a problem both in taste and color compared with the commercially-available salt-reduced say sauce and containing the coffee bean extract as a preventive, ameliorant or remedy for hypertension was obtained. The using amount of this say sauce is about 20 g/day, similar to the ordinarily employed one.

Capability of Exploitation in Industry

The preventive, ameliorant or remedy for hypertension according to the present invention is excellent in both blood pressure lowering action and blood pressure rise inhibiting action, and has high safety.

What is claimed is:

1. A soy sauce, comprising a raw coffee bean extract, said soy sauce comprising:
   a) chlorogenic acid; and
   b) caffeine;
wherein the chlorogenic acid and caffeine is contained in the raw coffee bean extract.

2. The soy sauce of claim 1, having a reduced salt content.

3. A method for treating hypertension in a mammal, which comprises
   administering to a mammal in need thereof an effective amount of the soy sauce of claim 1.

4. The method of claim 3, wherein said mammal is human.

5. A method of treating hypertension in a human, which comprises administering to a human in need thereof an effective amount of a soy sauce comprising a raw coffee bean extract, said extract comprising:
   a) chlorogenic acid; and
   b) caffeine,
wherein the chlorogenic acid and the caffeine are present in a chlorogenic acid/caffeine ratio of at least 4.8.

6. The soy sauce of claim 1, wherein the chlorogenic acid/caffeine weight ratio is 2 or greater.

7. The soy sauce of claim 1, wherein the chlorogenic acid/caffeine weight ratio is from 2 to 1,000.

8. The soy sauce of claim 1, wherein the raw coffee bean extract is obtained from beans of C. arabica.

9. The soy sauce of claim 1, wherein the raw coffee bean extract is obtained from beans of C. robusta.

10. The soy sauce of claim 1, wherein the raw coffee bean extract is obtained from beans of C. liberica.

11. The soy sauce of claim 1, wherein the raw coffee bean extract is obtained from beans of C. arabusta.

12. The soy sauce of claim 1, wherein the raw coffee bean extract is produced by solvent extraction of coffee beans.

13. The soy sauce of claim 1, wherein the raw coffee bean extract is produced by supercritical fluid extraction of coffee beans.

14. The soy sauce of claim 1, wherein the chlorogenic acid/caffeine weight ratio is from 2.5 to 500.

15. The soy sauce of claim 1, wherein the chlorogenic acid/caffeine weight ratio is from 2.5 to 100.

16. The soy sauce of claim 1, wherein the chlorogenic acid comprises 3-caffeoylquinic acid, 4-caffeoylquinic acid, 5-caffeoylquinic acid or mixtures thereof.

17. The soy sauce of claim 1, which further comprises one or more other additives comprising antihypertensive agents or vitamins.

* * * * *